(12) United States Patent
Ketterling et al.

(10) Patent No.: US 9,295,448 B2
(45) Date of Patent: Mar. 29, 2016

(54) METHODS FOR DIAGNOSING VITREO-RETINAL DISEASE

(71) Applicants: Jeffrey A. Ketterling, New York, NY (US); Jonathan Mamou, New York, NY (US); Ronald H. Silverman, New York, NY (US); Jerry Sebag, Laguna Beach, CA (US)

(72) Inventors: Jeffrey A. Ketterling, New York, NY (US); Jonathan Mamou, New York, NY (US); Ronald H. Silverman, New York, NY (US); Jerry Sebag, Laguna Beach, CA (US)

(73) Assignees: Riverside Research Institute, New York, NY (US); The Trustees of Columbia University in the City of New York, New York, NY (US)

(*) Notice: Subject to any disclaimer, the term of this patent is extended or adjusted under 35 U.S.C. 154(b) by 73 days.

(21) Appl. No.: 14/209,864

(22) Filed: Mar. 13, 2014

(65) Prior Publication Data
US 2014/0268036 A1 Sep. 18, 2014

Related U.S. Application Data

(60) Provisional application No. 61/779,484, filed on Mar. 13, 2013.

(51) Int. Cl.
*A61B 3/10* (2006.01)
*A61B 3/00* (2006.01)
*A61B 8/10* (2006.01)
*A61B 8/08* (2006.01)

(52) U.S. Cl.
CPC ............... *A61B 8/10* (2013.01); *A61B 8/5223* (2013.01)

(58) Field of Classification Search
USPC .................................................. 351/200–246
See application file for complete search history.

(56) References Cited

U.S. PATENT DOCUMENTS

| | | | |
|---|---|---|---|
| 6,039,691 A | 3/2000 | Walker et al. | |
| 6,238,342 B1 | 5/2001 | Feleppa et al. | |
| 6,312,383 B1 | 11/2001 | Lizzi et al. | |
| 6,949,071 B1* | 9/2005 | Saied et al. | 600/445 |
| 2002/0095087 A1 | 7/2002 | Mourad et al. | |
| 2005/0251043 A1 | 11/2005 | Saied et al. | |
| 2007/0239007 A1 | 10/2007 | Silverman et al. | |
| 2008/0004527 A1 | 1/2008 | Coleman et al. | |
| 2008/0309881 A1* | 12/2008 | Huang et al. | 351/246 |
| 2010/0211408 A1* | 8/2010 | Park et al. | 705/3 |
| 2011/0299034 A1* | 12/2011 | Walsh et al. | 351/206 |

OTHER PUBLICATIONS

PCT International Search Report and Written Opinion, Jul. 28, 2014, pp. 1-9, ISA/US.
Silverman R.H. et al. "Pulse-Encoded Ultrasound Imaging of the Vitreous With an Annular Array", Opthalmic Surgery, Lasers & Imaging, 2012, pp. 82-86, vol. 43, No. 1, USA.
Coleman. D. et al. "Ultrasonic Evaluation of the Vitreous and Retina", Seminars in Opthamology, 1998, pp. 210-218, vol. 13, No. 4, USA.

* cited by examiner

*Primary Examiner* — Mohammed Hasan
(74) *Attorney, Agent, or Firm* — Keith D. Nowak; Carter Ledyard & Milburn LLP

(57) ABSTRACT

A quantitative method to analyze phase-resolved, raw backscatter echo data or the envelope of phase-resolved, raw backscatter echo data to characterize vitreous inhomogeneities as they relate to normal aging and vitreo-retinal disease. The technique can be applied to 2D or 3D data acquired from the vitreous. The approach provides an objective end value to characterize the vitreous and provide a tool for early diagnosis, monitoring and planning treatment of vitreo-retinal diseases.

20 Claims, 4 Drawing Sheets

FIG. 1A  FIG. 1B  FIG. 1C  FIG. 1D
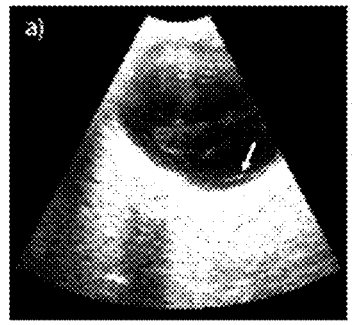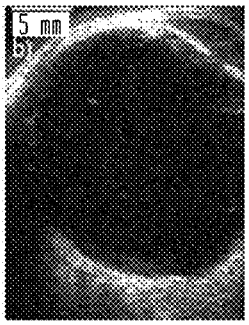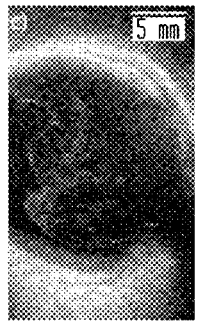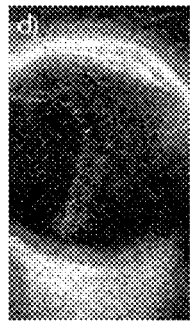
FIG. 2A  FIG. 2B  FIG. 2C
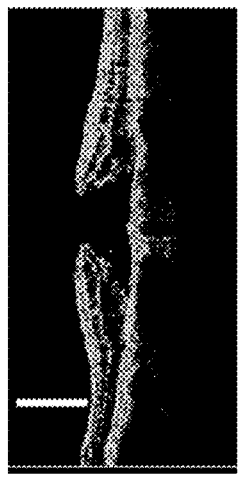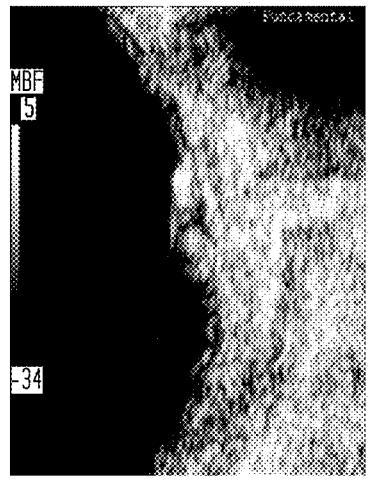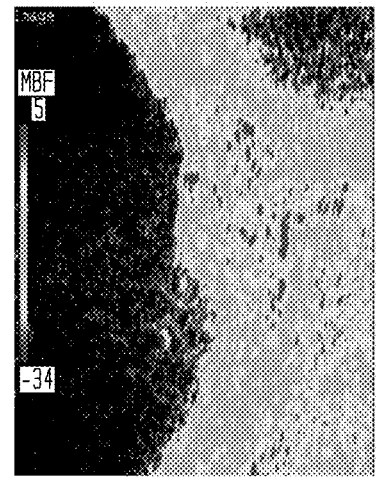

a) OD TRANSVERSE b) OD LONGITUDINAL c) OD LMAC

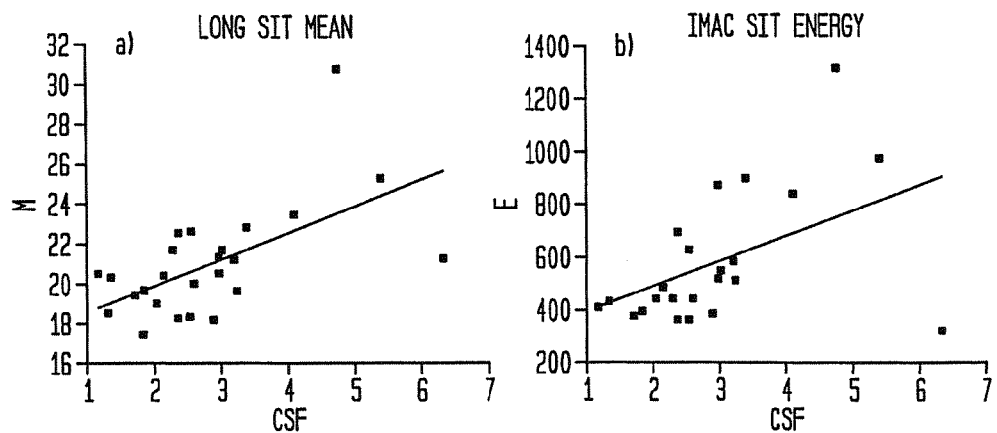
FIG. 6A
FIG. 6B
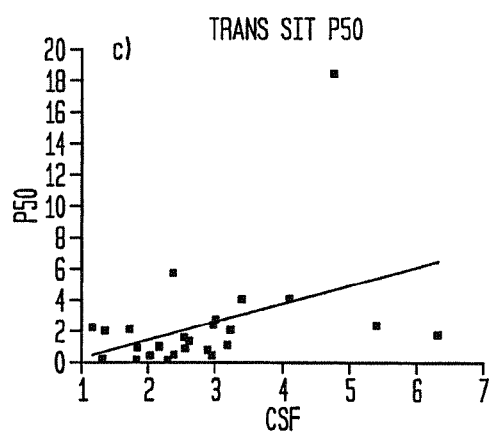
FIG. 6C

METHODS FOR DIAGNOSING VITREO-RETINAL DISEASE

BACKGROUND OF THE INVENTION

The young, healthy vitreous is a homogeneous, optically transparent gel filling the posterior segment of the eye. Gel vitreous volume increases during the first decade while the eye is growing in size and then remains stable until about the age of 40 years, when it begins to decrease in parallel with an increase in liquid vitreous. Macromolecular changes occurring during this process result in inhomogeneities within the vitreous. Concurrently, changes occurring at the vitreo-retinal interface allow the posterior vitreous cortex to detach from the internal ILL of the retina. When liquefaction and dehiscence occur simultaneously and in concert, the result is an innocuous posterior vitreous detachment (PVD). When the natural processes do not occur in concert, an anomalous PVD (APVD) may develop. The ability to diagnose precursors of APVD and to differentiate normal changes in vitreous related to aging from abnormal changes would permit early intervention before vitreo-retinal diseases progress to an advanced state. This would have a significant clinical impact by decreasing the likelihood of blindness, and reducing the cost of treatment and the risk to patients associated with advanced disease states. More broadly, early diagnosis has the potential to impact therapeutics of systemic diseases of the body such as diabetes.

The most clinically significant vitreo-retinal disease is diabetic retinopathy. The increased glucose levels in the vitreous of diabetic subjects have been shown to be associated with increased nonenzymatic glycation products and elevated levels of cross-linking and aggregation of vitreous collagen fibrils. Alteration of the vitreous due to poor glycemic control can extend or contract the vitreous hyaluronan, induce an APVD. and predates by years the optically visible evidence of retinal disease such as microhemorrhages, microaneurysms, leakage with hard exudates (detectable by examination and photography), and edema or neovascularization (detectable by fluorescein angiography). Unfortunately, because no current diagnostic technology is able to detect the precursors of diabetic retinopathy, the disease is typically only detected in the aforementioned advanced states at which point treatments are costly, difficult to implement, carry some risk to patient or may be too late to prevent blindness. The ability to detect and quantify the macromolecular and physiopathologic abnormalities of the vitreous much earlier in disease progression would permit better disease management, reduce ultimate treatment cost, and reduce the ultimate risk blindness.

Another vitreo-retinal disease affecting a significant number of patients is high myopia (exceeding −6 diopters), which has a 4% prevalence in the general population. Biochemical studies in myopic human eyes found a decreased collagen content and concentration in the central vitreous. The vitreous body in myopia becomes liquefied and contains filaments with localized nodules. The formation of liquid vitreous in myopia markedly destabilizes vitreous and threatens the retina because this process occurs relatively early in life and is not concurrent with dehiscence at the vitreo-retinal interface. This is different from the mechanism of vitreous liquefaction seen in aging, wherein the increase in liquid vitreous volume occurs in synchrony with decreased adhesion of vitreous to retina. The increased rate of liquefaction in high myopia leads to an increased incidence of PVD that typically occurs 5 to 10 years earlier than age-normal subjects. Myopic patients have a much greater risk of retinal detachment and, without treatment, blindness. A non-invasive diagnostic tool that does not require dilation that is capable of characterizing changes to the vitreous that signal a risk in a given individual, would permit early intervention.

Floaters are a common complaint related to myopia, PVD, and vitreous liquefaction/collagen aggregation due to aging, inflammation, and diabetes. Floaters move with vitreous displacement during ocular saccades and scatter incident light, casting a shadow on the retina that is perceived as a hair-like structure. PVD may also induce a glare caused by light scattering from condensed vitreous fibers, the detached posterior vitreous cortex, glial tissue of epipapillary origin adherent to the posterior vitreous cortex, or intravitreal blood. However, nothing is known about the size, number, or location of floaters as they relate to disease progression and normal aging.

To more effectively diagnose, treat, and ultimately prevent disorders of the vitreous, a rapid, safe, reproducible, and objective way to quantify the state of opacification (i.e., inhomogeneity) of the vitreous is needed. This approach differs from typical ophthalmic ultrasound devices that are designed to image the front or back of the eye rather than the vitreous. Because inhomogeneities within the vitreous are non-uniformly distributed, the method to quantify inhomogeneities would ideally make use of data obtained throughout the vitreous volume. Optical coherence tomography (OCT) permits visualization of abnormalities in the vicinity of the vitreo-retinal interface, but does not permit assessment of peripheral retinal pathology or imaging of the sclera and orbital tissues, nor does it allow assessment of motility of vitreous membranes in response to saccades, which is readily accomplished with real-time ultrasound. Ultrasound permits visualization of the entire vitreous and is sensitive to micro-scale (on the order of 20 μm) tissue properties related to changes in mass density and speed of sound (e.g., liquefaction vs. normal vitreous) and particle size and particle concentration (e.g., collagen aggregation, cell migration and proliferation within certain regions of the vitreous body.

SUMMARY OF THE INVENTION

A quantitative approach to characterize vitreous inhomogeneities (i.e., changes in acoustic impedance related to local properties and acoustic scatterers) in terms of contrast, size, shape and distribution is described. In one embodiment the imaging modality employed may be ultrasound, specifically ultrasound with high-frequency, 20 MHz annular-array transducer. The methods could be translated to any imaging modality that provides image data with sufficient contrast within the vitreous. The technique can be applied to 2D image planes of the full globe in one embodiment, or 3D volume data that has been assembled from a series of 2D image planes. The methods provide an objective means of characterizing the vitreous and represents a tool for early diagnosis, monitoring and planning treatment of vitreo-retinal diseases. The final step of the invention delivers at least one global parameter related to vitreous inhomogeneities and the pathologic state of the imaged eye. The global parameter can be used to diagnose vitreous conditions ranging from normal to various stages of malady. The diagnosis may be arranged to identify health or malady based on age.

Standard ultrasound images (i.e., B-mode) are representations of microstructure variations in the acoustical impedance of tissue. The images are qualitative because much of the information content of the acoustic waves is not utilized when forming B-mode images and each operator is free to adjust system settings (e.g., time-gain control, focus, acoustic power, etc.) to what they consider ideal. A standard B-mode image is formed by displaying the log-compressed envelope of the phase-resolved signal which removes the phase information. The goal of quantitative ultrasound (QUS) methods is to process raw, phase-resolved backscatter data in a system- and user-independent fashion in order to derive, by definition, quantitative estimates of acoustical and tissue properties.

Considerable research and development in QUS for biomedical applications has occurred over the past three decades. QUS methods to estimate speed of sound, density, attenuation, elastic properties of tissue, average scatterer size and acoustic concentration, and spectral parameters related to some defined bandwidth of the ultrasound transducer, such as the midband fit, intercept, and slope, have also been developed and successfully used for quantifying tissue properties. Here, QUS methods will be employed to derive at least one global parameter that permits the differentiation between vitreo-retinal disease and normal aging. The global parameter will ultimately be used to characterize vitreous inhomogeneities and diagnose vitreo-retinal diseases at an early state before outcomes, such as blindness, become unavoidable.

In one embodiment, data may be collected using a five-element, 20 MHz, high-frequency annular array. The data are collected by transmitting on a single element of the array and then the phase-resolved backscatter echo is digitized on all five elements simultaneously. By rapidly repeating this process on all five elements, the transmit-to-receive echo signals are acquired for all twenty-five possible combinations of the five-element array. These transmit-to-receive echoes are then beamformed with a synthetic-focusing approach that greatly improves signal to noise, depth of field (DOF) and resolution compared to the standard, single-element-transducer method of current clinical ophthalmic ultrasound. Additional information on synthetic-focusing approach can be found in co-pending U.S. application Ser. No. 13/655,086 entitled "SYNTHETIC-FOCUSING STRATEGIES FOR REAL-TIME ANNULAR-ARRAY IMAGING", which is incorporated by reference.

Once data are acquired using an ultrasound approach, a normalization step is performed to the raw data in order to remove system and user dependence. The normalization step requires the use of a well-calibrated ultrasound scattering phantom (USP). The phantom consists of spherical mono-dispersed particles of known size distribution and known acoustic properties that are randomly and uniformly located in a background media of known acoustic properties. Normalization data are acquired from the USP using the same system and system settings as those used to acquire clinical data. These data are processed and used to remove system and user dependence from the data acquired using the ultrasound approach of the present invention. The vitreous is segmented out from the surrounding tissue so that the resulting normalized data only contain information about the vitreous. The transmission of at least one ultrasound signal, the acquisition of backscatter of the transmitted signal and normalization of the acquired data results in the creation of one unit. The step of creating one unit may be repeated.

Following normalization, various QUS techniques, as well as common image processing methods, are applied to the phase-resolved or envelope-detected data to extract clinically relevant local-level region of interest (ROI) estimates and then global parameters that relate to scatterer size, scatterer concentration, location within vitreous, spatial distribution, etc. Through the scanning and analysis of data from many patients, a database of global parameters is compiled of changes related to normal aging vs. disease-related changes. In addition to the global parameters obtained from the ultrasound backscatter signal, non-ultrasound global parameters that represent clinical information, such as age, pre-existing conditions (e.g., myopia), blood sugar level, etc., may also be entered into the database.

Using well-known classification methods, the collection of global parameters can be combined in different ways to establish a correlation between the global parameters and the health/state of the vitreous. Ultimately, at least one global index or end value can be employed to diagnose the health of the vitreous, the effect of treatment, or the progression of disease. In some embodiments, global parameters could be the global index or end value.

BRIEF DESCRIPTION OF THE DRAWINGS

FIG. 1A shows B-mode imaging of a human subject following posterior-vitreous detachment with a conventional single-element 10 MHz probe.

FIG. 1B shows synthetically focused image of the same eye obtained with a 20 MHz annular array using monocycle excitation.

FIGS. 1C and 1D show synthetically-focused images obtained with a 20 MHz annular array using chirp excitation.

FIGS. 2A to 2C show a macular hole image from optical coherence tomography, B-mode ultrasound and a midband-fit QUS parameterization of the raw B-mode image data.

FIGS. 6A to 6C show illustrative scatter plots with best-fit linear regressions for three selected cases of Table I.

DESCRIPTION OF THE INVENTION

Figure 3A:
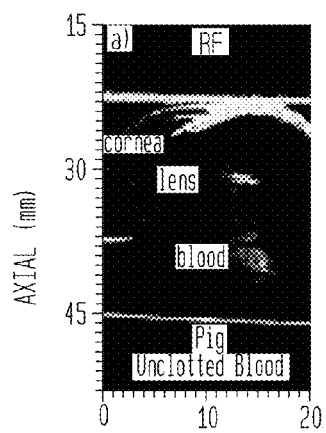
FIGS. 3A to 3D show annular-array images of ex vivo pig eyes into which blood had been introduced to simulate vitreous hemorrhage.
Figure 3B:
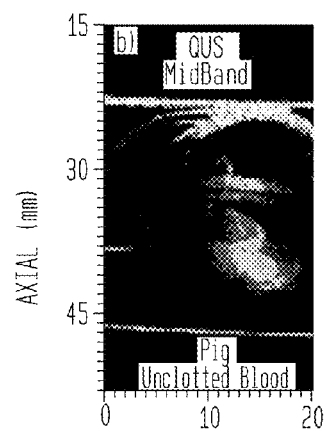
Figure 3C:
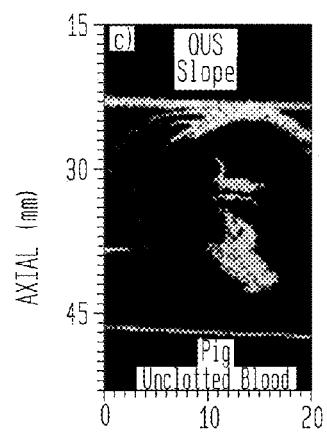
Figure 3D:
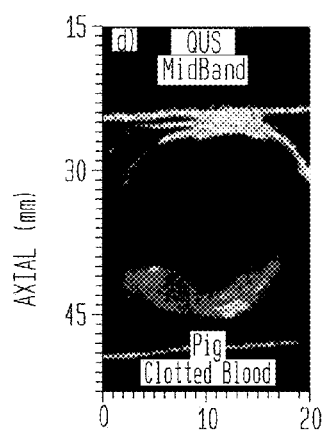
Figure 3E:
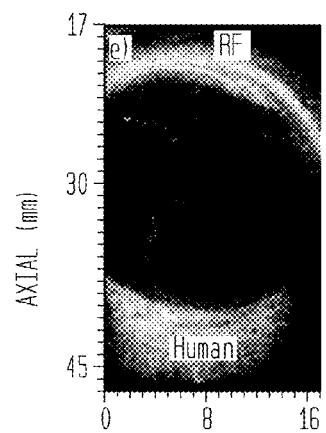
FIGS. 3E and 3F are a B-mode and QUS (midband fit) image examples from a human eye scanned with the 20 MHz array.

The image data required to implement the proposed method to characterize the vitreous is not necessarily restricted to a single imaging modality as long as the modality can provide a form of raw, time-resolved digitized image information. In one embodiment ultrasound is used, specifically an annular-array imaging approach using a five-element, 20 MHz transducer. Relative to single-element transducers, annular arrays provide superior, DOF and resolution. These properties are highly advantageous for the detection of inhomogeneities throughout the whole vitreous. The radial symmetry of the acoustic field, common acoustic propagation path of all array elements, and reduction in system complexity provide significant advantages compared to other ultrasound approaches. The methods that follow are described as they apply to data obtained with an ultrasound method. The approach will provide the first objective means of characterizing the vitreous in a quantitative fashion and will represent a powerful tool for early diagnosis, monitoring and planning treatment of vitreo-retinal diseases.

Image-Data Acquisition

In one embodiment, a real-time, annular-array ultrasound system that implements a synthetic-focusing approach is used to acquire data of the vitreous. The system may have a lateral scan length of up to 22 mm and operate at real-time frame rates [FIGS. 1A-D and 3E]. The transducer may operate at 20 MHz, have five annular elements, a 1 cm total aperture, and a 31 mm geometric focus. A synthetic-focusing approach (single transmit and five receive to acquire all 25 transmit-to-receive combinations) is used to simulate the appropriate time delays necessary to focus to some arbitrary depth. This method of synthetic-focusing beamforming is more versatile than the more traditional dynamic-focusing approach (five transmit and five receive when using a five-element annular array) because an arbitrary number of focal zones can be synthesized with only five transmit events. The set of 25 acquired transmit-to-receive events can be reduced for more efficient processing with minimal loss in image quality. Additional information on synthetic-focusing approach can be found in co-pending U.S. application Ser. No. 13/655,086 entitled "SYNTHETIC-FOCUSING STRATEGIES FOR REAL-TIME ANNULAR-ARRAY IMAGING", which is incorporated by reference. A further benefit of the annular array imaging approach is that low contrast vitreous inhomogeneities, such as PVD and floaters are better resolved [FIGS. 1B-D and 3E] than with current clinical imaging approaches [FIG. 1A].

The ultrasound data digitized from the annular array is saved as raw, phase-resolved backscatter echo data sampled at a rate appropriate for the transducer bandwidth. The data could be obtained with impulse excitation or coded excitation (e.g., chirp). As is commonly known in the art, coded excitation schemes have the advantage of improved penetration depth and sensitivity with only a minimal loss to image quality. The data acquired from the eye are typically in a single plane to provide 2D data. In one instance, this 2D data represents the full cross section of the globe. By acquiring 2D image planes while rotating the imaging probe or translating the probe in the cross-plane direction, 3D volumetric data set can also be assembled. The spacing between image lines and image planes may be, in one embodiment, less than the acoustic beamwidth of the transducer. Various means for mechanically scanning the ultrasound probe are possible, although a hand-held approach is most advantageous. An acoustic coupling medium will be used between the ultrasound probe and eye.

An ultrasound annular array has a particular advantage for the proposed application because all of the array elements propagate along the same acoustic axis that minimizes the chance of beamforming errors caused by acoustic refraction. In addition, an annular array has a radial acoustic beam profile that provides in plane and out of plane resolution that is identical. Finally, the processing of the echo data with delay and sum synthetic focusing results in an averaging of the electronic background noise with a resulting improvement in signal contrast. For imaging the vitreous, signal contrast is essential because the inhomogeneities are weak scatterers.

QUS Methods

Conventional B-mode images are derived from the log-compressed envelope of raw phase-resolved backscatter echo data which results in loss of frequency-dependent information. QUS methods applied to backscatter echo data, particularly when the phase information is retained, represent a robust approach to obtain quantitative estimates of acoustical and material properties of tissue in a system- and user-independent fashion.

To effectively implement QUS processing, a signal normalization step is applied to remove the influence of the transducer, system, and user from the backscatter echo signals. This step ensures the QUS methods yield uniform properties as a function of depth so that QUS estimates reflect physical changes in scatterer concentration, size, and spatial organization rather than system and user factors. A well-calibrated scattering phantom that contains known concentrations of mono-disperse scatterers ranging from 10 to 100 µm (i.e., glass beads or polystyrene spheres) may be used for this step and the process is well known in the art. Using the annular array, the backscatter coefficient is calculated throughout the phantom, accounting for attenuation, and then fit to a scattering model (e.g., Gaussian form factor or a straight-line fit) to yield QUS estimates. This process normalizes the backscatter echo data from array such that backscatter values are uniform throughout the phantom. Next, backscatter data are obtained from unknown test phantoms (i.e., additional phantoms with known scatter sizes and concentrations). Because the theoretical backscatter coefficient from the agar phantoms is well-defined and easily obtained using Faran theory, the normalized annular-array results from the unknown phantom can be compared to and validated against theoretical predictions. The annular-array backscatter values can also be compared to those obtained with a single-element transducer normalized using the echo from a rigid, planar reflector.

Before applying QUS methods to characterize vitreous inhomogeneity, the vitreous is segmented out from surrounding tissue (i.e., sclera, retina, etc.) The segmentation of the vitreous removes the potential contribution from tissue outside of the vitreous and allows for the additional calculation of normalized parameters relative to vitreous volume or cross-sectional area within each image plane. For example, a segmentation approach can be used that uses the generalized Hough transform to find an arc of a circle within the 2D images. It is understood that other commonly used segmentation approaches could also be used.

Figure 3F:
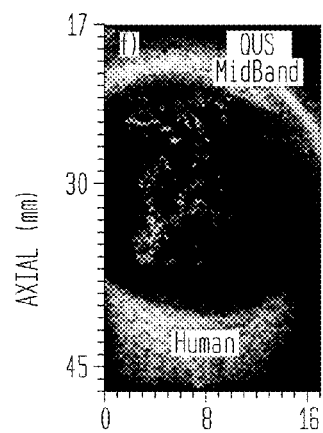

A next step of processing the raw, phase-resolved backscatter is to calculate QUS estimates from overlapping (local) regions of interest (ROIs) that are on the order of 5-20 acoustic wavelengths. The normalized spectrum of the ROI is obtained by averaging the spectrum of each echo segment within the ROI and compensating for attenuation and system dependence. Then the normalized spectra are fit to a chosen ultrasound scattering model (e.g., Gaussian form factor or straight-line fit), and the fit parameters represent the QUS estimates. The estimates can be displayed as a parameter image or converted into a color map and overlaid back onto a conventional, grey-scale, B-mode image (FIG. 3F), but these approaches do not yield a global index or end value of vitreous health. However, unlike a B-mode image, the QUS estimates can be related back to fundamental tissue properties related to microstructure. Additional QUS estimates can be derived from the envelope of the phase resolved backscatter echo data by using envelope-statistic models (e.g., Nakagmi, Homodyne-K, etc.). The normalization approach for these envelope-statistic models differs from that of the backscatter approach, wherein each envelope model requires a normalization specific to envelop model.

QUS-Based Classification Of The Vitreous

After calculating the local-level ROI estimates from the raw phase-resolved backscatter data and/or envelope data, the overall collection of local-level ROI estimates can be further processed to derive a collection of clinically relevant global parameter that combine and reduce the collection of local-ROI QUS estimates related to vitreous inhomogeneities in 2D image planes or a 3D volume derived from 2D image planes. Examples of specific quantities to compute are gross size. shape (i.e., linear, circular or focal), location (i.e., close to macula), distribution, and relative concentration (based on dimensional scale, shape, etc.) of inhomogeneities. Because it is not necessarily possible to know a priori which parameters are most relevant to a specific vitreo-retinal disease, the described approach will generate a diverse set of global parameters. These can then be related to age-normal and disease patients after implementing a classifier analysis.

Clinically-based, non-ultrasound-based information such as the standardized NEI Visual Function Questionnaire (VFQ)-25 or vision contrast sensitivity function can also be included for classifier analysis with the set of global parameters. By working with a variety of ultrasound and non-ultrasound global parameters, the optimal combination of global parameters for characterizing the vitreous can be determined. In this invention, the optimal combination of all global parameters for a given eye will be incorporated into a classifier in order to yield at least one optimal global index or end value that is indicative of overall vitreous pathology. As is well known in the art, it is also possible to generate color-coded parameter images that can replace or overlay a standard B-mode grey scale image. However, while these images provide quantitative information on a local level, they do not provide a global index or end value that represents the state of the vitreous.

The diverse set ultrasound and non-ultrasound of parameters will be used in conjunction with age-normal patient data to train sophisticated classifiers (e.g., linear-discriminant, neural-networks, and support vector-machine approaches) for detecting and characterizing inhomogeneity within the vitreous. Support-vector machines provide the most flexibility in classifier design at the expense of increased computational requirements. These classifiers easily isolate parameters that significantly contribute to the characterization of the vitreous and allow for the removal of less relevant parameters. After classification analysis, at least one global index or end value that indicated the state of the vitreous will be produced.

FIGS. 3A-F show an example of local-ROI QUS analysis applied to 20 MHz annular-array data acquired from an excised pig eye and a human subject using the straight-line fit scattering model (i.e., midband and slope parameters). Blood that contained an anti-clotting agent (EDTA) (FIGS. 3A-C) was injected into the vitreous of one pig eye, and clotted blood (FIG. 3D) into another eye. The phase-resolved backscatter echo data from the vitreous were analyzed with QUS methods and the local-ROI QUS estimates were overlaid onto the B-mode image. The same color range was used for the midband cases and the images revealed a difference between the clotted and unclotted case. For the midband images, the clotted case had an overall lower magnitude for the region of blood than did the unclotted. For the human eye example, the B-mode image (FIG. 3E) showed debris in the eye and a PVD. The midband local-ROI QUS estimates overlay (FIG. 3F) showed debris in the eye and a differentiation from the normal vitreous. FIG. 2C shows a similar example of QUS-visualized debris in the vitreous in a patient with a macular hole.

EXAMPLE 1

One example of a method to characterize inhomogeneities of the vitreous is provided. First, phase-resolved echo data are acquired from planes within the vitreous using a 20 MHz, high-frequency-ultrasound annular array. Planar sections are acquired in a series of parallel planes such that a 3D volume is sampled. Next, the data are normalized and processed to obtain local-ROI QUS estimates. The large collection of local-ROI estimates are reduced to a set of global parameters that have clinical relevance related to the state of the vitreous. The global parameters along with relevant non-ultrasound clinical global parameters obtained from numerous patients are entered into a database. The database contains cases of normal vitreous at various ages and disease cases. Using the global parameters in the database, a classifier is trained to distinguish between healthy vitreous and vitreo-retinal disease. Once the classifier is trained, a look-up table can be created such that new global parameters obtained from a patient with unknown vitreous state can be used to generate at least one global index or end value that indicates whether the vitreous is healthy or diseased. For instance, a database could be created from patients with myopia. Global parameters from the new patient may be entered in the classifier and analyzed against the myopia database to produce at least one global index or end value that would indicate if the vitreous was healthy or diseased, and if diseased, the severity or level of progression of myopia.

In another exemplary use of the invention, a database of vitreous parameters from normal vitreous at various ages is compared to a database of vitreous from myopes at various ages to determine if disease is present or progressing. This example is provided with reference to an ultrasound approach that detects changes related to density, speed of sound and scatterer properties. This example should not be limited to a single approach, as other imaging approaches would detect other material properties. For instance, an optical technique could detect spectral absorption or scattering from vitreous inhomogeneities.

The above example is provided with reference to an ultrasound backscatter approach that is sensitive to tissue properties related to density, speed of sound and scatterer properties. The invention should not be limited to one ultrasound imaging approach or to one imaging modality as other imaging modalities may provide raw, phase-resolved information or envelope data related to other material properties. For instance, an optical technique could detect spectral absorption or scattering from vitreous inhomogeneities.

EXAMPLE 2

In another embodiment of the invention, image-processing methods are employed to derive global index or end value of inhomogeneities (floaters) in patients who are candidates for vitrectomy. Patients could have developed floater etiologies related to posterior vitreous detachment, myopic vitreopathy or other common conditions of the eye.

An ophthalmic, clinical ultrasound unit with a single-element, 15-MHz transducer with a 20-mm focal length and 7-mm aperture is used to acquire 100 image frames of log-compressed envelope data before scan conversion and video display. These data are digitally sampled at 40-MHz with 8-bit accuracy before envelope detection. All the settings on the ultrasound machine are kept the same in order to allow for direct comparison between patients. An exam was then performed by placing the ultrasound probe directly on the globe at the limbus, to avoid attenuation by the eyelid and lens and to minimize trauma to the cornea.

Figure 4A:
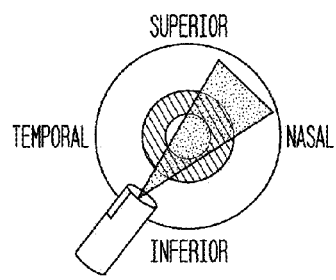
FIGS. 4A to 4C show B-mode ultrasonography performed at three positions (nasal longitudinal, inferotemporal longitudinal and inferotemporal transverse.
Figure 4B:
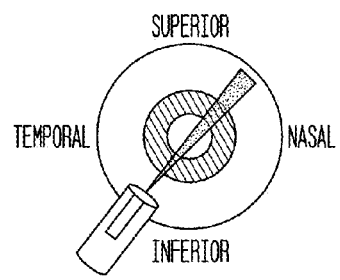
Figure 4C:
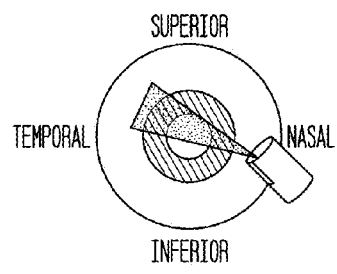
Figure 5A:
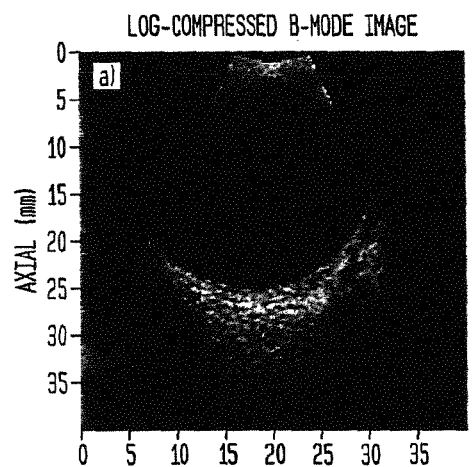
FIG. 5A shows a sector-scan, ultrasound B-mode image taken at standardized settings: (100 total frames acquired at 16 frames/second, 40 mm image depth, sector scan, 1024× 170 pixel image.)

As illustrated in FIGS. 4A-C, B-scan ultrasonography is performed at three positions (nasal longitudinal, inferotemporal longitudinal and inferotemporal transverse) using standardized settings: (100 total frames acquired at 16 frames/second, 40 mm image depth, sector scan, 1024×170 pixel image; FIG. 5A). For the inferotemporal scans, subjects are asked to look supratemporally and inferonasally to induce vitreous displacement. The first position, nasal longitudinal, results in a view of the macula. The latter two inferotemporal positions provide views of the 1:30 clock hour OD (right eye) or 10:30 clock hour OS (left eye). The nasal longitudinal and the two inferotemporal positions are referred to as "imac", "trans", and "long", respectively.

Figure 5B:
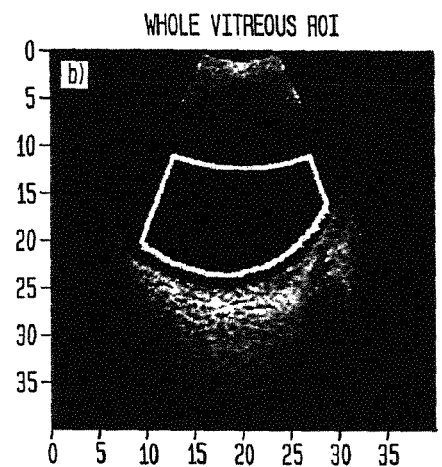
FIG. 5B shows a first region of interest that includes the entire vitreous within the DOF of the ultrasound image.
Figure 5C:
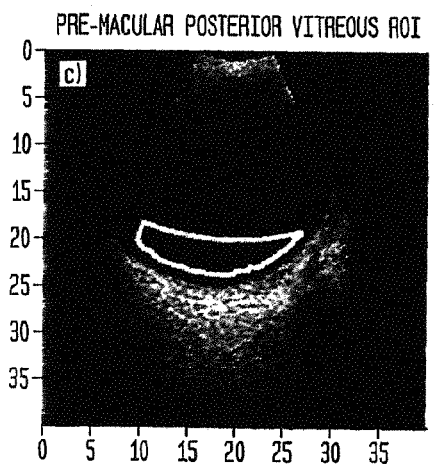
FIG. 5C shows a second region of interest that is smaller and entirely included in the first region of interest.

The image stacks of 100 images are manually inspected and only artifact-free frames are processed. In this example, the image pixels represent the local-level ROI estimates. Within each artifact-free frame, two distinct global-parameter ROIs are automatically selected. The first ROI includes the entire vitreous within the DOF of the ultrasound image (FIG. 5B). The second ROI is smaller and entirely included in the first ROI (FIG. 5C). The global-parameter ROIs are termed whole-central vitreous ROI and premacular posterior vitreous ROI, respectively. The whole central vitreous ROI is started at a depth of 11.7 mm. The premacular ROI was started at a depth of 19.5 mm.

Each ROI is processed to yield three distinct global parameters: energy (E), mean (M), and P50. E is defined as the sum of the squared acoustic values within the ROI divided by the ROI size. M is the mean of the acoustic values divided by the ROI size. P50 is obtained by computing the percentage of the ROI filled by clusters of echogenic regions greater in size than 50 pixels (0.069 mm$^2$) in this example. The global parameters are averaged over the number of artifact-free frames available for the corresponding ultrasound data. Normal vitreous is typically hypoechoic and will yield low values for the global parameters, whereas floaters are hyperechoic and will yield increased values of global parameters.

After processing, statistical analyses are performed to assess whether the global parameters are able to quantify the eye function (i.e., the ability to see contrast) perceived by the patient. In this example, the statistical analysis represents the classifier analysis.

The contrast sensitivity function (CSF), which represents the relationship between contrast sensitivity and spatial frequency, is recorded for each patient and represents the patient's subjective evaluation of their floaters on vision function. CSF, expressed in % W, typically increases in eyes of patients complaining of vitreous floaters. Pearson correlation and associated p values are computed between global parameters and CSF value for each eye, scan direction and ROI. Pearson correlation is deemed significant if the p value is <0.05. For this study, each eye is treated as independent even in the case where two eyes from the same patient are processed. Each eye is also independently evaluated for CSF.

Results

TABLE 1 displays the Pearson correlations and associated p values for each global parameter, scan position and ROI. The results for the whole-central ROI show that all correlations but one (P50 in the trans direction) are significant with p values smaller than 0.021; the p value obtained for P50 in the trans scan position is just above 0.05. The best correlation value is obtained for M in the long position and a slightly lower value is obtained for E in the long position. Table I shows that for all QUS estimates, the correlation value obtained in the long direction is larger than those obtained in the other two scanning directions. For the whole-central ROI, all the remaining significant correlation values are between 0.45 and 0.50. The correlation values obtained for the premacular posterior ROI are smaller than the corresponding values for the whole-vitreous ROI. None of the corresponding p values are below the significance threshold. In this example, the whole-central, long-position, M, E, and P50 global parameters would be retained as the final global indexes or end values.

TABLE 1

Pearson correlations p values for each global parameter, scan position ROI.

|  |  | E imac | E long | E trans | M imac | M long | M trans | P50 imac | P50 long | P50 trans |
|---|---|---|---|---|---|---|---|---|---|---|
| Whole-central ROI | R | 0.496 | 0.576 | 0.459 | 0.471 | 0.595 | 0.495 | 0.472 | 0.497 | 0.394 |
| Whole-central ROI | p | 0.012 | 0.003 | 0.021 | 0.018 | 0.002 | 0.012 | 0.017 | 0.012 | 0.051 |
| Premacular posterior ROI | R | 0.376 | 0.351 | 0.246 | 0.364 | 0.352 | 0.271 | 0.352 | 0.337 | 0.175 |
| Premacular posterior ROI | p | 0.064 | 0.086 | 0.237 | 0.074 | 0.084 | 0.189 | 0.085 | 0.1 | 0.403 |

FIG. 6A-C shows illustrative scatter plots with best-fit linear regressions for three selected cases of Table I. FIG. 6A shows the best correlation result (0.595 with p <0.002) obtained for the whole-central ROI, M and the trans position. Overall, the plots show a good linear fit, except for two eyes with CSF values >4.5%W. FIG. 6B shows an intermediate case with a correlation value of 0.496 and p<0.012 obtained for the whole-central ROI, E, and the long position. The data points are more scattered around the linear regression than in FIG. 6A and the same two eyes with large CSF values are also far from the linear regression. Finally, FIG. 6C shows the only non-significant result obtained for the whole-central ROI (P50 in the trans position).

While the present invention has been described in conjunction with specific embodiments, those of normal skill in the art will appreciate the modifications and variations can be made without departing from the scope and the spirit of the present invention. Such modifications and variations are envisioned to be within the scope of the appended claims.

The invention claimed is:

1. A method to acquire and process vitreous image data to characterize vitreous inhomogeneities comprising the steps of:
   creating a unit, said creating a unit comprising transmitting at least one ultrasound signal, acquiring phase-resolved, raw backscatter echo data of said transmitted signal, and normalizing said acquired data, wherein said normalized acquired data forms said unit; the method further comprising:
   extracting local level estimates from said normalized data; and
   processing said extracted local level estimates, said processing producing at least one global parameter, said at least one global parameter being used to objectively characterize one or more vitreous inhomogeneities.

2. The method of claim 1, wherein said global parameter is produced from one local-level estimate from within a vitreous of an eye.

3. The method of claim 1, wherein said global parameter is produced from a plurality of local level estimates from within a vitreous of an eye.

4. The method of claim 1, further comprising repeating the step of creating a unit until 2D single cross-sectional image-plane data of an entire vitreous is obtained.

5. The method of claim 4, further comprising preparing an image volume by compiling a plurality of said 2D single cross-sectional image plane data.

6. The method of claim 1, wherein said ultrasound signal is transmitted from an annular array.

7. The method of claim 6, further comprising applying a synthetic focusing approach to said acquired data.

8. The method of claim 1, further comprising calculating an envelope of said phase-resolved, raw backscatter echo data.

9. The method of claim 1, wherein said ultrasound signal is transmitted from a single-element.

10. The method of claim 1, further comprising a step of segmenting the vitreous out from surrounding tissue prior to extracting local-level estimates.

11. A method to quantify vitreous image data to characterize inhomogeneities of a vitreous comprising the steps of:
    transmitting at least one ultrasound signal;
    acquiring an envelope of phase-resolved, raw backscatter echo data of said transmitted signal;
    normalizing said acquired data;
    extracting local level estimates from said normalized data; and
    combining said local level estimates producing at least one global parameter used to characterize vitreous inhomogeneities, said at least one global parameter being incorporated into a classifier to yield at least one optimal global index or end value indicative of an overall vitreous pathology.

12. The method of claim 11, further comprising creating a normal database, wherein said normal database is a compilation of first extracted global parameters being vitreous parameter data representing a normal vitreous.

13. The method of claim 12, further comprising creating a disease database, wherein said disease database is a compilation of second extracted global parameters being vitreous parameter data representing diseased vitreous conditions at various stages of disease.

14. The method of claim 13, wherein said at least one global parameter is compared with said normal database and said disease database, said comparison identifying a correlation between said global parameter and information in one of two said databases, said correlation being used to diagnose one or more vitreous conditions ranging from age-normal to various stages of diseased states, said diagnosis being further comparable with said optimal global index or end value.

15. A method to quantify vitreous image data to characterize vitreous inhomogeneities comprising the steps of:
    creating a unit, said creating a unit comprising transmitting at least one ultrasound signal, acquiring phase-resolved, raw backscatter echo data of said transmitted signal, and normalizing said acquired data;
    extracting local-level estimates from said normalized data;
    combining said extracted local-level estimates producing at least one global parameter, said at least one global parameter being incorporated into a classifier to yield an end value indicative of an overall vitreous pathology;
    creating a normal database, wherein said normal database is a compilation of first extracted global parameters being vitreous parameter data representing normal vitreous;
    creating a disease database, wherein said disease database is a compilation of second extracted global parameters being vitreous parameter data representing diseased vitreous conditions at various stages of disease; and
    diagnosing a vitreous condition based on comparison of said normal database with said disease database.

16. The method of claim 15, further comprising repeating the step of creating a unit until 2D single cross-sectional image plane data of an entire vitreous is obtained.

17. The method of claim 16, further comprising preparing an image volume by compiling a plurality of said 2D single cross-sectional image plane data.

18. The method of claim 15, wherein said at least one transmitted ultrasound signal is transmitted from an annular array.

19. The method of claim 18, further comprising applying a synthetic focusing approach to said acquired backscatter signal.

20. The method of claim 18, further comprising calculating an envelope of said phase-resolved, raw backscatter echo data.

* * * * *